United States Patent [19]

Zmora

[11] Patent Number: 6,028,909
[45] Date of Patent: Feb. 22, 2000

[54] METHOD AND SYSTEM FOR THE CORRECTION OF ARTIFACTS IN COMPUTED TOMOGRAPHY IMAGES

[75] Inventor: Ilan Zmora, Skokie, Ill.

[73] Assignee: Kabushiki Kaisha Toshiba, Kawasaki, Japan

[21] Appl. No.: 09/025,238

[22] Filed: Feb. 18, 1998

[51] Int. Cl.[7] ........................................................ A61B 6/03
[52] U.S. Cl. .................................. 378/15; 378/4; 378/901
[58] Field of Search ..................................... 378/4, 15, 901

[56] References Cited

U.S. PATENT DOCUMENTS

| | | | |
|---|---|---|---|
| 5,825,718 | 10/1998 | Ruth et al. | 378/19 |
| 5,848,117 | 12/1998 | Urchuk et al. | 378/19 |

OTHER PUBLICATIONS

Principles of computerized tomographic imaging, Kak, et al., (relevant pages, 49–112), Institute of Electrical and Electronics Engineers, Inc. NY 1988.

Practical cone–beam algorithm, Feldkamp, et al., J. Opt. Soc. Am. A/vol. 1, No. 6, Jun. 1984, pp. 612–619.

Computed tomography scanning with simultaneous patient translation, Crawford, et al., Med. Phys. 17(6), Nov./Dec. 1990, pp. 967–982.

Cone beam tomography with circular, elliptical and spiral orbits, Yan, et al., Phys. Med. Biol., 1992, vol. 37, No. 3, pp. 493–506.

Multi–slice helical CT: Scan and reconstruction, Hui Hu, Med. Phys. 26(1), Jan. 1999, pp. 5–18.

New, efficient Fourier–reconstruction method for approximate image reconstruction in spiral cone–beam CT at small cone angles, Schaller, et al., Abstract, 12 pages. No Date.

Algorithm for image reconstruction in multi–slice helical CT, Taguchi, et al., Medial Physics, vol., 25, No. 4, Apr. 1998, pp. 550–561.

Primary Examiner—David Vernon Bruce
Attorney, Agent, or Firm—Oblon, Spivak, McClelland, Maier & Neustadt, P.C.

[57] ABSTRACT

A method and system for the correction of artifacts in computed tomography ages. Artifacts may occur at a crossover channel in computed tomography images. Sets of interpolation data about the crossover channel and extended interpolation data are generated as extensions of the interpolation data. The extended interpolation data overlaps with a portion of the interpolation data. The overlapping portion includes the crossover channel where the artifact may occur. The overlapping portion is determined by threshold channels which may be automatically selected by the system according to the invention. In this overlapping portion, feathering weights are applied to the interpolated data and the extended interpolated data. New data values are defined to using the feathering weights which eliminate the crossover artifact and produce continuous data. The feathering weights are chosen to meet certain criteria.

55 Claims, 4 Drawing Sheets

(10 ROWS)

(1000 ELEMENTS)

METHOD AND SYSTEM FOR THE CORRECTION OF ARTIFACTS IN COMPUTED TOMOGRAPHY IMAGES

CROSS-REFERENCE TO RELATED APPLICATIONS

The present application is related to application Ser. No. 08/675,832 and application Ser. No. 08/675,833, the disclosures of which are herein incorporated by reference.

BACKGROUND OF THE INVENTION

1. Field of the Invention

The present invention relates to the correction of artifacts in computed tomography and, in particular, to the correction of artifacts in helical multi-slice computed tomography.

2. Description of the Related Art

Commonly existing single slice CT systems employ an array of x-ray detectors which extend a line or an arc in the transverse plane (the transverse plane is also called the scan plane or the X-Y plane). The x-ray source is collimated in such a way as to limit the x-ray radiation only to the detector array. As a result of this geometry, in the static scan mode the data collected by the detector array during one revolution of the x-ray source and the x-ray detectors pertains to one plane which is defined by the x-ray focal spot and the array of detectors, and the ensuing image shows a cut through the scanned object at this same plane.

In the helical scan mode, the object moves in the axial direction during the scan, so that the data collected during the scan corresponds to longer axial length, however the data is still collected along the same plane in space, although the object is now in motion relative to this plane.

In order to speed up the process of data collection, x-ray CT cone beam multi-slice systems were developed having multi-slice arrangement of detectors. This multi-slice arrangement of detectors can be obtained by actually stacking several layers of detector arrays in the axial direction, or by using other area detectors such as x-ray image intensifier and more. The x-ray source is now collimated as to allow the x-ray radiation to be collected by all the area of detector arrays thus covering a larger volume than in the case of single slice systems. Multi-slice scanners can be used in the static mode, covering larger volume in one scan, but their largest advantage is achieved in helical scans where the gain in the speed along the axial direction will be proportional to the number of slices.

The "cone beam" part in the name of the described systems refers to the fact that radiation of the x-ray source extends a cone-like portion of space, or in other words, the radiation diverges from one spot. Consequently, the planes defined by the different detector arrays and the focal spot (detection planes), are not parallel to each other, but also converge towards the x-ray focal spot.

The last fact, the convergence of the detection planes, is currently a weakness of x-ray CT cone beam multi-slice systems, because images generated with the commonly available reconstruction algorithms sometimes result in several types of artifacts in the images. One of the ways to reduce those artifacts is the generation of finite width images which are processed by filtered interpolation. The complimentary data rebinning is used, both in the regular generation of zero width images or in the generation of finite width images, in order to improve the spatial resolution in the axial direction. However the addition of the complimentary data results in artifacts.

To better illustrate how these artifacts arise, it is useful to consider multi-slice image generation. In fan beam multi-slice CT, the reconstruction of an image is typically preceded by slice data generation (SLG). The slice data (SD) generated at this stage is a set of data which is designed to approximate a set of two dimensional data that would have been collected in a stationary two dimensional scan at a specific image plane. Consequently the SD are arranged in SD fan-views which are generated from the acquisition data, better known as projection data, which is the acquired data after the necessary corrections and processing. The acquisition data belonging to every detector line are arranged in acquisition fan-views, where each acquisition fan-view contains one data point corresponding to each channel, ordered according to channel numbers or channel angles. All these data points within an acquisition fan-view are acquired at the same time, and therefore have the same axial position which depends on the view angle. The axial position assigned to all the points (regardless of channel number) within an acquisition fan view $V_n$, with fan-view angle $\alpha_n$, and acquired by detector line k, is given by the following expression:

$$Z(V_n, m) = Z_{0k} + P \times \frac{\alpha_n}{2\pi} \qquad (1)$$

where P is the helical pitch, which is the axial distance traveled by the scanned object during one full rotation (360 degrees) of the x-ray tube, and $Z_{0k}$ is the initial (at the beginning of the rotation) axial position of the kth detector line.

The fact that the SD is designed to approximate the data that would have been collected in a stationary two-dimensional scan at a specific user-determined axial position, and, on the other hand, each acquisition fan-view corresponds to a different axial position, explains why some interpolation processing with respect to the axial direction is required.

The interpolation processing can be simple linear interpolation, or higher order interpolation, when the reconstructed image plane is a thin plane (zero reconstruction width) defined by one point on the Z axis, or it can be filtered interpolation processing (discrete filtering or continuous filtering), when the reconstructed image plane is thick and defined by its center and its reconstruction width. As a concrete example, the description will concentrate on linear interpolation in the generation of thin slices, but the treatment of the other cases can be derived from the same principles. For example, in the case of the discrete filtering, the same description applies to each of the thin slices involved in the filtering, and the same correction has to be applied to each of these thin slices.

As explained above, when only direct data is involved in the SLG, all the acquisition data points in each acquisition fan-view, or SD fan-view, correspond to the same axial position, irrespective of the channel number. The situation is more complicated when complementary data (reflection data, or opposite data) are incorporated in the SLG. As each direct data point involved in the SLG can be characterized by belonging to detector line k, fan-view $V_n$ with fan angle $\alpha_n$, and channel angle $\beta_m$, the corresponding complementary data point is then defined as belonging to the same detector line k, with opposite channel angle $-\beta_m$, and belonging to an acquisition fan-view defined by its angle as $\alpha_n + 2\beta_m + \pi$. This transformation from direct data point to its complimentary data point can be summarized:

$$(\alpha_n, \beta_m) \rightarrow (\alpha_n + 2\beta_m + \pi, -\beta_m)$$

The last result shows that the complimentary data points involved in the generation of the SD at a specific SD fan-view, belongs to many different acquisition fan-views, and therefore these points correspond to different axial positions. The fact that in general the new fan-view angles do not correspond to real acquisition fan-view angles is corrected by interpolation using the real acquisition fan-views.

Figure 1:
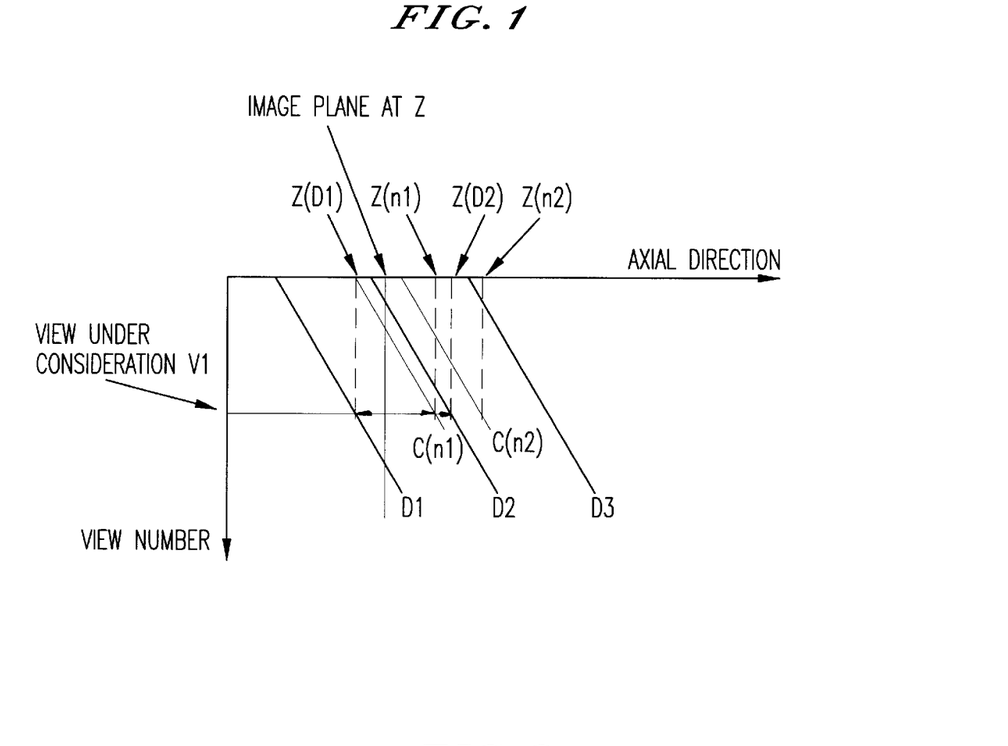
FIG. 1 is a graph illustrating the axial location of acquisition data points.

To understand how these facts result in a discontinuity refer to FIG. 1, which shows the axial positions of the acquisition data points under consideration as a function of the SD view number, or view angle. The graphical consequence of the constant axial motion, the fact that the acquisition data points within a fan-view are all taken at the same time, and the fact that the acquisition fan-view are collected in succession in time is that the lines representing the positions are tilted with a constant slope with respect to the axial position and view angle axes. This slope is determined by Equation 1 given above. The full lines represent the positions of the direct data D1, D2, and D3, for all channel numbers, and the broken lines which are tilted with the same slope, correspond to the positions of the complimentary data points. Contrary to the direct data lines, each channel number is represented by a different broken line. Consequently the broken line denoted by C(n1) corresponds to a certain channel number n1, and the broken line denoted by C(n2) corresponds to another channel number n2. More generally, the dependence of the axial position of the complimentary points belonging to one acquisition fan view (and one detector segment) on their channel number, is linear dependence. This dependence can be described as motion with respect to the axial position of the direct data points in the same view which do not depend on the channel number and therefor do not move. At certain scan parameters the position of the opposite data can cross over the position of the direct data. The channel at which this cross-over occurs is a point of discontinuity in the slice data. For the purpose of this demonstration, the axial positions of the data points will be denoted as Z(D1), Z(D2), and Z(D3), for the direct data D1, D2, and D3, respectively, and Z(n1), and Z(n2) for the complimentary points, C(n1) and C(n2). The vertical line is drawn at the axial position Z, of the image plane, and the intersection of this line with the horizontal line that is drawn through V1, determines the interpolation point for all the channels in view V1. Since the positions of the data points depend on the channel number, the interpolation operation also depends on the channel number.

For channel n1 the result of the calculated value D(Z,V1, n1) is obtained by linear interpolation with D1 and C1–D (Z,V1,n1)=LI(Z(D1),Z(n1),Z,D1,C(n1)), where LI is the linear interpolation operation. The first step implied by the equation above is the identification of Z(D1) and Z(n1) as the two closest neighbor points on both sides of Z, and the application of the linear interpolation, follows as the second step:

$$(x1, x2, x, D1, D2) = \frac{x2-x}{x2-x1}D1 + \frac{x-x1}{x2-x1}$$

where x1 and x2 are, by definition, the closest points on both sides of point x, and D1 and D2 are the data corresponding to them.

For channel n2 the result of the calculated value D(Z,V1, n2) is obtained by linear interpolation with D1 and D2–D (Z,V1,n2)=LI(Z(D1),Z(D2),Z,D1,D2).

Here, in the calculation for n2, the two points on both sides of Z are Z(D1) and Z(D2), the reason being that at some intermediate point between n1 and n2, the line representing the axial position of the complimentary data points crossed the line of the direct data point Z(D2).

Denoting now

Figure 2:
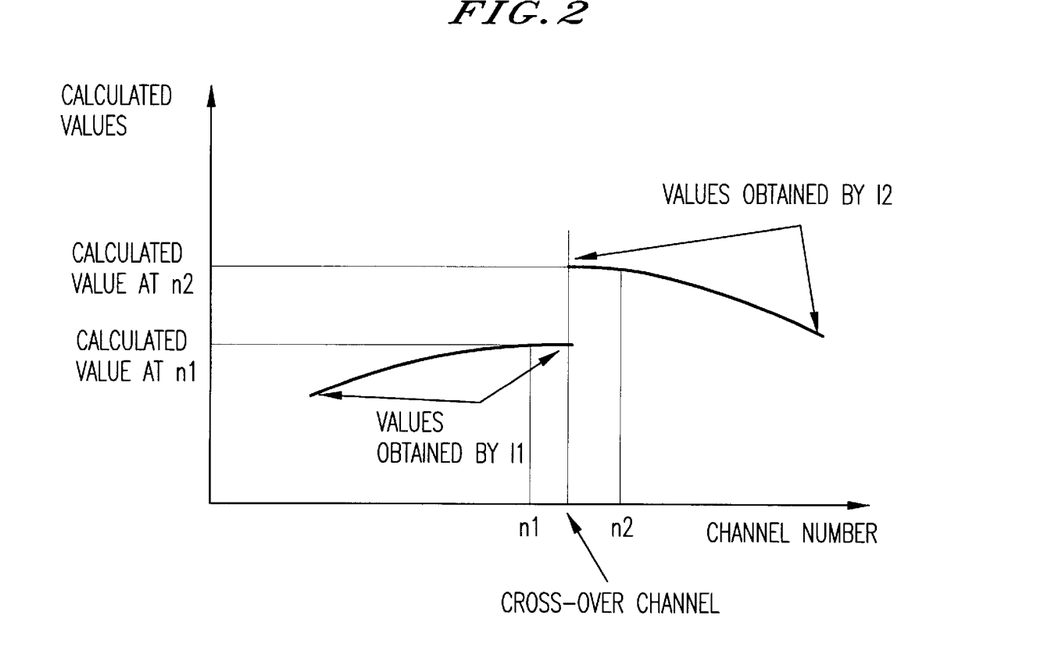
FIG. 2 is a graph illustrating a discontinuity in calculated values of slice data according to the prior art.

I1(ni)=D(z,v1,ni) for ni<n1 and,

I2(nj)=D(z,v1,nj) for nj>n2, it can be seen that the difference between the result for I1 and the result for I2 is that, I1 (an interpolated set of data) depends on complimentary value C(n1), while I2 (another interpolated set of data) depends in the same way on D2. Due to the cone angle, data value D2 and data value C(n1) may not belong to the same detector angle and they are generally not equal, so that the data obtained in I2 is not a smooth continuation of the data obtained by I1. The occurrence of the discontinuity between I1 and I2 is shown in FIG. 2, which shows the two sets of calculated values as a function of the channel number. This manifests itself as streaks in a high density object in the image. The problem is that I1 is performed for some range of channels n where n<n1, and I2 is performed for some range channels n where n>n2.

SUMMARY OF THE INVENTION

It is an object of the present invention to solve an image quality problem that arises in the image generation process in X-ray CT.

Another object of the present invention is to improve image quality in helical multi-slice CT.

A further object of the invention is to improve image quality in helical multi-slice CT when the image generation process uses complimentary rebinning and interpolations in the axial direction.

These and other objects of the invention are achieved by a method and system which generates interpolated data which is feathered using feathering weights. The interpolated data may consist of first and second interpolated data having an overlapping range. The range may include a crossover channel. The range may be determined by selecting first and second threshold channels about the crossover channel. The data is feathered in the overlapping range, which can eliminate a cross-over artifact.

The feathering is carried out using feathering weights which meet certain conditions. One condition is that the weight for the first and second interpolated data at the crossover channel are both equal to, or approximately equal to each other. The feathering weights can also be determined as a function axial distance, where the weights at the crossover distance are both equal to, or approximately equal to each other.

In the invention extended interpolation data may be generated as extensions of the interpolated data. In one example, first and second interpolation data is generated, and first and second extended interpolation data is generated as extensions of the first and second interpolation data, respectively. The first extended interpolation data overlaps a portion of the second interpolation data and the second extended interpolation data overlaps a portion of the first interpolation data. The feathering is carried out in the overlapping portions.

The invention can be advantageously used in an imaging processing device having a helical scanner. An interpolation circuit may be connected to the helical scanner. The circuit may include an interpolated data generation circuit, which may be used to generate both interpolated data and extended interpolated data, a threshold channel selection circuit, which may be used to select threshold channels, and a feathering circuit which may be used to carry out feathering preferably using feathering weights.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying draws, wherein.

DESCRIPTION OF THE PREFERRED EMBODIMENT

Figure 3:
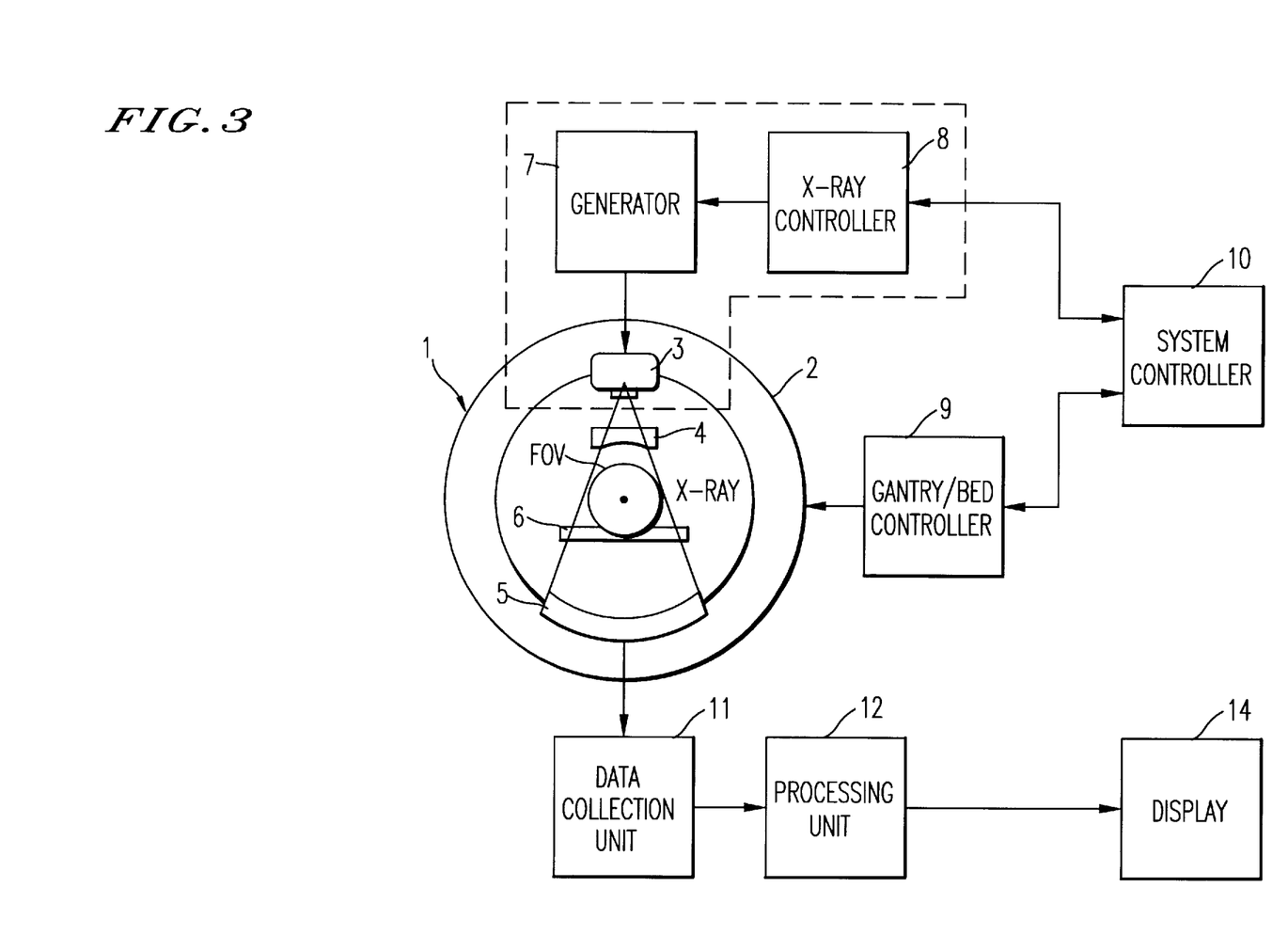
FIG. 3 is a diagram of a computed tomography system according to the invention.
Figure 4:
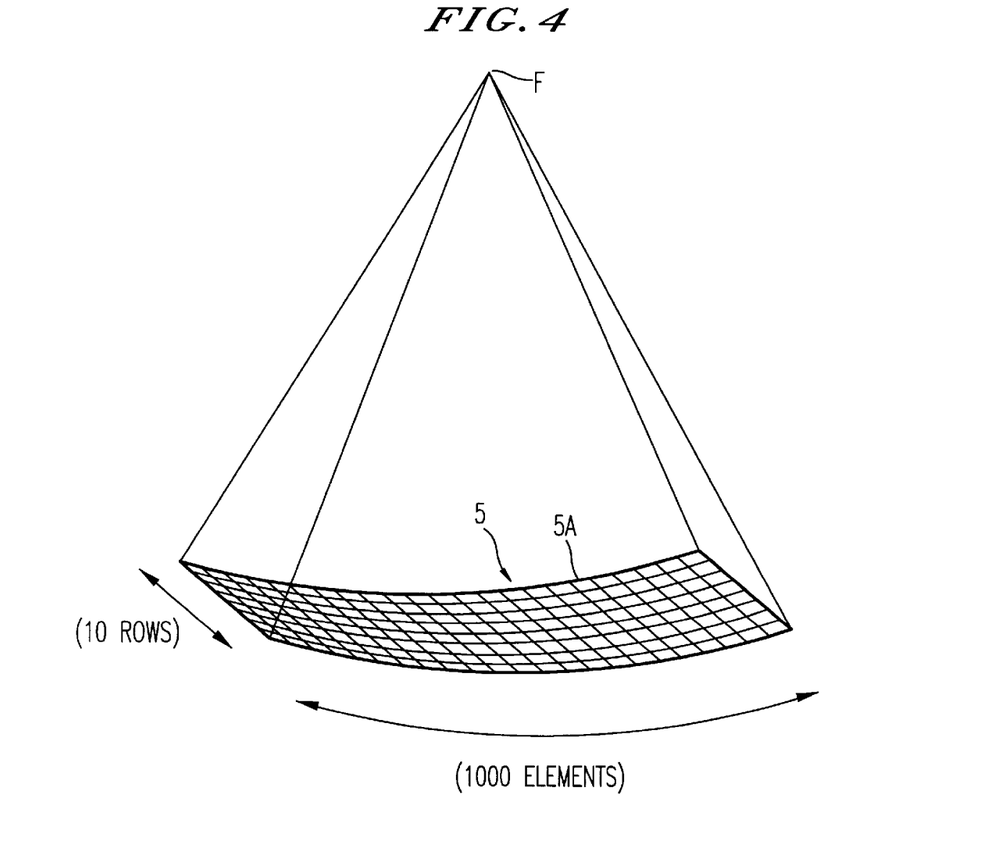
FIG. 4 is a diagram of the two-dimensional detector array of FIG. 1.
Figure 5:
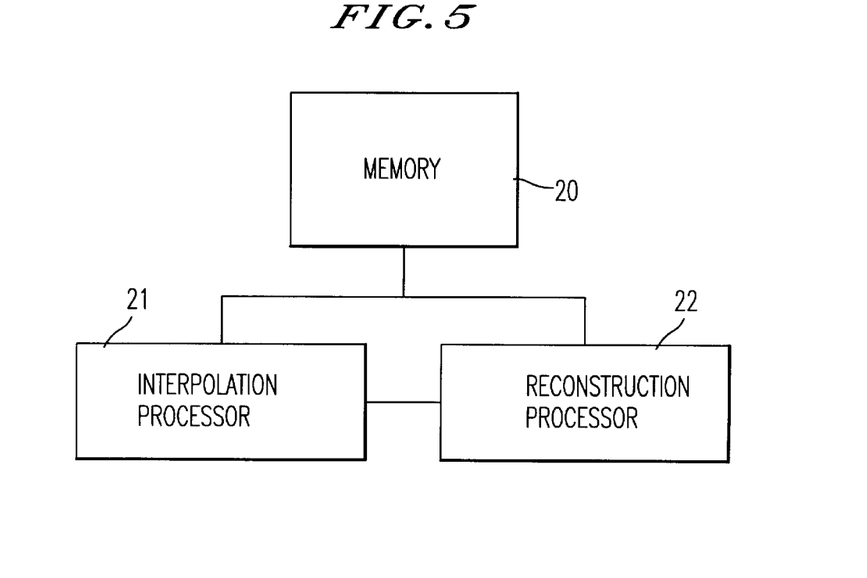
FIG. 5 is a diagram of the processing unit according to the invention.

With reference to the drawings, particularly FIG. 3, a first embodiment of the invention will be described. FIG. 3 shows an x-ray computed topographic imaging device according to a first embodiment of this invention. FIG. 4 is a perspective view of a two-dimensional array type detector of FIG. 3. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements 5A arranged in two-dimensional fashion, i.e., a plurality of elements arranged in one dimension stacked in a plurality of rows. In FIG. 5, ten rows each having 1000 elements are shown (other arrangements are possible), with the x-ray flux shown schematically emitted from focal point F.

X-ray source 3 and two-dimensional array type x-ray detector 5 are installed on a rotating ring 2 facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to processing unit 12. Processing unit 12 uses the projection data to reconstruct the image. The projection data is interpolated to correct for discontinuities, and the interpolated or corrected data is then sent to a reconstruction processor where a reconstruction operation is performed.

FIG. 5 shows in more detail an embodiment of the processing unit 11. Unit 11 contains an interpolation processor 21 and a reconstruction processor 22. Unit 11 can contain memory 20 to store data, intermediate values, etc. used or generated by processors 12 and 22.

Processing unit 12 generates three-dimensional image data or tomographic image data and sends the data to display/output device 14, where it is displayed visually or output as a three-dimensional image or tomographic image.

For the reconstruction processing in the generation of multi-slice images, there are there are two commonly available methods: multi-slice fan beam reconstruction and multi-slice cone beam (Feldkamp) reconstruction, although other methods may be used. These two methods of reconstruction differ by the way in which the Z-dependence of the raw data and the images is treated in the reconstruction. Both reconstruction methods can be used to generate either zero width images or to generate finite width images. Both methods can use complimentary data rebinning to improve the axial resolution, however it is more complicated in the Feldkamp reconstruction than in the fan beam reconstruction. If complimentary data rebinning will be used in the Feldkamp reconstruction, the cross-over artifact will appear in the images.

In the present invention, the reconstruction processor can implement any desired reconstruction processing. The description will use the fan-beam reconstruction technique to illustrate the principles of the invention. However, the invention is not limited to this one example. Also, the present invention is applicable to either zero-width or finite-width images. The finite-width images can be processed with either discrete or continuous filtered interpolation.

Since the reconstruction techniques are known to those skilled in the art, description pf them will be omitted here. Descriptions of the techniques can be found, for example, in Feldkamp et al., J. Opt. Soc. Am., vol. 1(A), pp. 612–619 (1984), Kak et al., *Principles of Computed Tomography*, IEEE Press (New York 1988), Crawford et al., Med Phys. 17(6), p.967 (1990), Yan et al., Phys. Med. Biol., No. 3, p. 493 (1992), and Schaller et al., SPIE, *Proceedings of the International Symposium on Medical Imaging*, p. 213 (1997).

Figure 6:
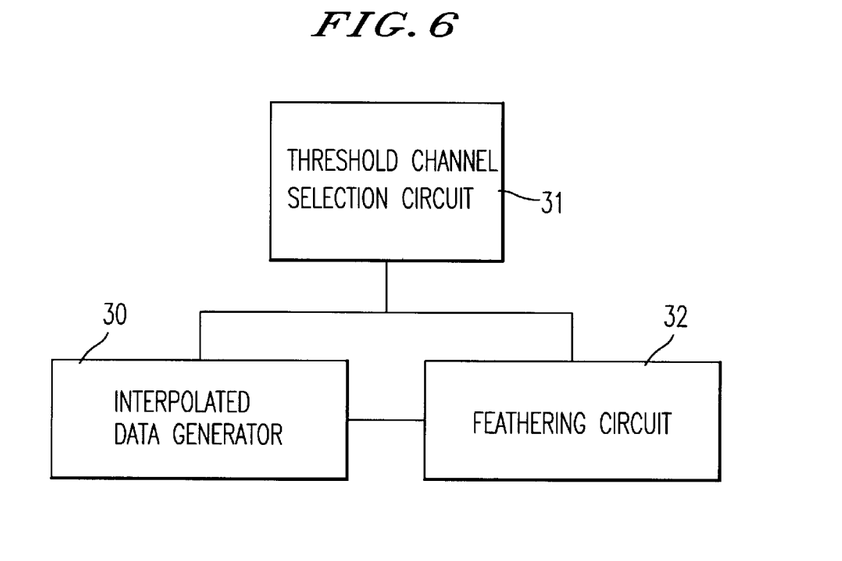
FIG. 6 is a diagram of the interpolation processor according to the invention.
Figure 7:
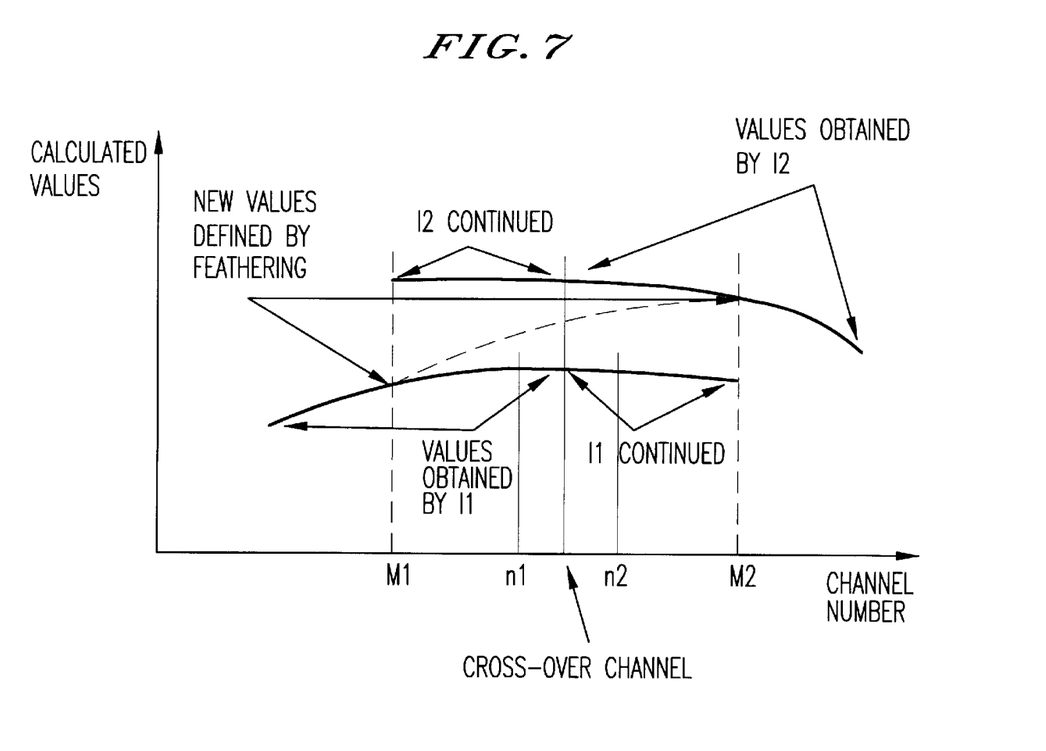
FIG. 7 is a graph illustrating calculated values of slice data according to the invention.

The interpolation processor 21 is shown in more detail in FIG. 6. An interpolated data generator 30 generates interpolated data from the projection data. The threshold channel selector circuit 31 selects threshold data channels over which extended interpolated data is generated by generator 30. Using the interpolated data, the extended interpolation data and the threshold channels, the feathering circuit 32 applies feathering weights and generates feathered data or corrected data which is used to eliminate artifacts. The procedures carried out by these circuits are illustrated by FIG. 7.

The operation of the device according to the invention will now be described in more detail. A subject is helically scanned using the device of FIG. 3 and multi-slice data is acquired. The data is then interpolated in interpolation processor 21. I1 and I2 are calculated in the extended regions, by ignoring the cross-over (see FIG. 7). Thus I1 which is calculated by continuing to use the relevant complimentary data point and its axial position despite the fact that, after the cross-over, this point is not the immediate neighbor of the axial position of the image plan. For example, the calculation of I1 for channel n2 which is in the extended range is:

I1(n2)=LI(Z(D1),Z(n1),Z,D1,C(n2)).

The calculation of I2 on the other hand, is done in the extended zone, by using the direct data point and its axial position, ignoring the fact that the complimentary data point is closer, in the axial direction, to the image plan. For channel n1, which is in the extended range of I2, the calculation is:

I2(n1)=LI(Z(D1),Z(D2),Z,D1,D2).

More generally, the definitions of I1, and I2 in their respective extended ranges are:

I1(n)=LI(Z(D1),Z(n1),Z,D1,C(n)), for n1<n<M2, and

I2(n)=LI(Z(D1),Z(D2),Z,D1,D2), for M1<n<n2.

M1 and M2 are threshold channels selected on the one hand taking into consideration the effectiveness of the correction, but also taking into consideration computational convenience.

The values of M1 and M2 can be symmetrically located around n1 and n2 and generally they are chosen so that n1−M1, and M2−n2 are minimal, but enough to avoid the cross-over artifacts. For a typical scanner with 896 channels per fan-view, an example for the choice of M1 and M2 in would be:

n1=M1=M2−n2=50.

M1 and M2 are preferably selected automatically but may be selected by the user via an interface, such as a keyboard, to system controller 10. The values I1 and I2 are then weighted, preferably using feathering weights, over the range of M1<n<M2.

The correction has the following form:

$D_c(Z, V1, n) = W1(n)I1(Z(n),Z(D1),Z,D1,C(n))+W2(n)I2(Z(D1),Z(D2),Z,D1,D2)$.

Here, $D_c$ is the corrected data, C(n) is the complimentary data value corresponding to any channel n, V1 is a view, and the feathering weights W1(n) and W2(n) and should be linear, higher order polynomials, or any functions of the channel number n which satisfy the following conditions:

1. W1 and W2 should be continuous functions of n.
2. W1(n)+W2(n)=1, for any M1<n<M2.
3. W1(M1)=W2(M2)=1.
4. $W1(n_c)=W2(n_c)=0.5$, where $n_c$ is the cross-over channel.

Condition 4 was chosen based upon the fact that there is typically not enough information to allow a preference of either of the 2 branches (I1 or I2) at the cross-over channel. Their average, or approximately their average, is thus a reasonable choice.

Other choices for condition 4 are possible, for example:

$W1(n_c)/W2(n_c)=A_d/A_c$, where $A_d$ is the cone angle of the detector line of the direct data and $A_c$ is the cone angle of the detector line of the complimentary data. This condition requires information about the cone angles of the corresponding channels.

In this formulation n is assumed to be a continuous variable which can take on any value in its range defined in condition 2. However, $n_c$, the cross-over channel is usually not an integer.

In a second example of the data interpolation according to the invention, the weights are expressed in terms of a naturally continuous variable, which is the axial distance d, between the axial position Z(n) of the complementary data point at channel n, and the axial position Z(M1) of the first threshold channel: d=Z(n)−Z(M1). In this case M1 and M2 do not have to be integers and the freedom in their position, can be used to conveniently locate Z(M1) and Z(M2) symmetrically around Z(D2). As functions of d, W1 and W2 have to obey similar conditions:

1. W1 and W2 should be continuous functions of d.
2. W1(d)+W2(d)=1, for any $0<d<d_{M2}$, where $d_{M2}$ is the distance Z(M2)−Z(M1).
3. $W1(0)=W2(d_{M2})=1$.
4. $W1(d_c)=W2(d_c)=0.5$, where $d_c$ is the cross-over distance Z(D2)−Z(M1).

The present invention can also be implemented in other configurations. For example, the helical scanning unit may be controlled by a personal or small computer and the data processing can be carried out by the computer. In this configuration, the computer could control the functions of system controller 10 as well as those of data collection unit 11 and processing unit 12.

With a computer-based system, the invention could be carried out using software. The invention could be programmed in the computer initially, or added later in an upgraded software package. Thus, the invention could also be in the form of software on a computer readable medium, such as a magnetic disk or optical disk.

What is claimed as new and desired to be protected by Letters Patent is:

1. An image processing device, comprising:
   a helical scanner; and
   an extended data range interpolation circuit connected to said scanner.

2. A device as recited in claim 1, wherein said interpolation circuit comprises:
   means for generating first interpolated data in a first data range containing a cross-over point;
   means for generating second interpolated data in a second data range containing said cross-over point;
   means for determining a portion of overlap of said first and second data ranges; and
   means for weighting, using feathering weights, said first and second interpolated data in said portion.

3. A device as recited in claim 2, comprising:
   said means for determining said portion between first and second threshold channels M1 and M2;
   said means for weighting using said feathering weights W1 and W2 satisfying:
   W1 and W2 are continuous functions of n;
   W1(n)+W2(n)=1, for any M1<n<M2;
   W1(M1)=W2(M2)=1; and
   $W1(n_c)=W2(n_c)=0.5$;
      where n is a data channel, $n_c$ is said cross-over channel, and M1 and M2 are said first and second threshold channels, respectively.

4. A device as recited in claim 3, comprising:
   said means for weighting using said feathering weights W1 and W2 satisfying $W1(n_c) \approx W2(n_c) \approx 0.5$.

5. A device as recited in claim 2, comprising:
   said means for determining said portion between first and second threshold channels M1 and M2; and
   said means for weighting using said feathering weights W1 and W2 satisfying:

W1 and W2 are continuous functions of d;
W1(d)+W2(d)=1, for $0<d<d_{M2}$;
W1(0)=W2($d_{M2}$)=1; and
W1($d_c$)=W2($d_c$)=0.5;
where Z(n) is an axial position of a complementary data point at channel n, Z(M1) and Z(M2) are axial positions of said first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

6. A device as recited in claim 5, comprising:
said means for weighting using said feathering weights W1 and W2 satisfying W1($d_c$)≈W2($d_c$)≈0.5.

7. A device as recited in claim 1, wherein said interpolation comprises:
means for generating first and second interpolation data;
means for selecting a first portion of said first interpolation data from a first data channel to a cross-over channel and from said cross-over channel to a first threshold channel;
means for selecting a second portion of said second interpolation data from a second data channel to said cross-over channel and from said cross-over channel to a second threshold channel; and
means for feathering an overlapping portion of said first and second portions.

8. A device as recited in claim 7, wherein said means for feathering comprises:
means for generating data D as:
D(Z, V1, n)=W1(n)I1(Z(n),Z(D1,Z,C(n),D1)+W2(n)I2(Z(D1,)Z(D2),Z,D1,D2);
where I1 and I2 are said first and second interpolation data, respectively, C(n) is a complimentary data value corresponding to a data channel n, V1 is a view, and W1(n) and W2(n) are feathering weights.

9. A device as recited in claim 8, wherein said feathering weights satisfy:
W1 and W2 are continuous functions of n;
W1(n)+W2(n)=1, for any M1<n<M2;
W1(M1)=W2(M2)=1; and
W1($n_c$)=W2($n_c$)=0.5;
where $n_c$ is said cross-over channel, and M1 and M2 are said first and second threshold channels, respectively.

10. A device as recited in claim 9, comprising:
said means for weighting using said feathering weights W1 and W2 satisfying W1($n_c$)≈W2($n_c$)≈0.5.

11. A device as recited in claim 8, wherein said feathering weights satisfy:
W1 and W2 are continuous functions of d;
W1(d)+W2(d)=1, for $0<d<d_{M2}$;
W1(0)=W2($d_{M2}$)=1; and
W1($d_c$)=W2($d_c$)=0.5;
where Z(n) is an axial distance of a complementary data point at channel n, Z(M1) and Z(M2) are axial positions of said first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

12. A device as recited in claim 11, comprising:
said means for weighting using said feathering weights W1 and W2 satisfying W1($d_c$)≈W2($d_c$)≈0.5.

13. A device as recited in claim 1, wherein said interpolation circuit comprises:

means for generating first interpolated data I1(n) in a first data channel range;
means for generating second interpolated data I2(n) in a second data channel range;
means for generating corrected data D as:
D(Z, V1, n)=W1(n)I1(Z(n),Z(D1,Z,C(n),D1)+W2(n)I2(Z(D1,)Z(D2),Z,D1,D2);
where C(n) is a complimentary data value corresponding to a data channel n, and W1(n) and W2(n) are feathering weights.

14. A device as recited in claim 13, wherein said feathering weights satisfy:
W1 and W2 are continuous functions of n;
W1(n)+W2(n)=1, for any M1<n<M2;
W1(M1)=W2(M2)=1; and
W1($n_c$)=W2($n_c$)=0.5;
where $n_c$ is a cross-over channel, and M1 and M2 are first and second threshold channels, respectively.

15. A device as recited in claim 14, comprising:
said means for weighting using said feathering weights W1 and W2 satisfying W1($n_c$)≈W2($n_c$)≈0.5.

16. A device as recited in claim 13, wherein said feathering weights satisfy:
W1 and W2 are continuous functions of d;
W1(d)+W2(d)=1, for $0<d<d_{M2}$;
W1(0)=W2($d_{M2}$)=1; and
W1($d_c$)=W2($d_c$)=0.5;
where Z(n) is an axial position of a complementary data point at channel n, Z(M1) and Z(M2) are axial positions of first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

17. A device as recited in claim 16, comprising:
said means for weighting using said feathering weights W1 and W2 satisfying W1($d_c$)≈W2($d_c$)≈0.5.

18. A device as recited in claim 1, wherein:
said interpolation circuit comprises a feathering circuit having feathering weights satisfying one of first and second sets of conditions, said first set comprising:
W1 and W2 are continuous functions of n,
W1(n)+W2(n)=1, for any M1<n<M2,
W1(M1)=W2(M2)=1, and
W1($n_c$)=W2($n_c$)=0.5; and
said second set comprising:
W1 and W2 are continuous functions of d,
W1(d)+W2(d)=1, for $0<d<d_{M2}$,
W1(0)=W2($d_{M2}$)=1, and
W($d_c$)=W2($d_c$)=0.5;
where n is a data channel of said scanner, $n_c$ is a cross-over channel, and M1 and M2 are first and second threshold channels, respectively, Z(n) is an axial position of a complementary data point at said channel n, Z(M1) and Z(M2) are axial positions of said first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

19. An image processing device, comprising:
a helical scanner; and
an interpolation circuit connected to said scanner comprising:
an interpolated data generation circuit,
a threshold channel selection circuit, and a feathering circuit.

20. A device as recited in claim 19, wherein said feathering circuit has feathering weights W1 and W2 satisfying:
   W1 and W2 are continuous functions of n;
   W1(n)+W2(n)=1, for any M1<n<M2;
   W1(M1)=W2(M2)=1; and
   W1($n_c$)=W2($n_c$)=0.5;
      where n is a data channel, $n_c$ is a cross-over channel, and M1 and M2 are first and second threshold channels, respectively.

21. A device as recited in claim 20, comprising:
   said feathering weights satisfying W1($n_c$)≈W2($n_c$)≈0.5.

22. A device as recited in claim 19, said feathering circuit has feathering weights W1 and W2 satisfying:
   W1 and W2 are continuous functions of d;
   W1(d)+W2(d)=1, for 0<d<$d_{M2}$;
   W1(0)=W2($d_{M2}$)=1; and
   W1($d_c$)=W2($d_c$)=0.5;
where Z(n) is an axial position of a complementary data point at channel n, Z(M1) and Z(M2) are axial positions of first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

23. A device as recited in claim 20, comprising:
   said feathering weights satisfying W1($d_c$)≈W2($d_c$) [|m]F0.5.

24. A device as recited in claim 19, wherein said interpolated data generation circuit comprises:
   means for generating interpolation data; and
   means for generating extended interpolation data.

25. A device as recited in claim 19, wherein said threshold channel selection circuit comprises:
   means for selecting a first threshold channel in a first set of interpolation data; and
   means for selecting a second threshold channel in a second set of interpolation data;
   said first and second threshold channels defining a feathering range.

26. A device as recited in claim 25, comprising:
   said feathering circuit feathering data in said feathering range.

27. A device as recited in claim 25, comprising:
   said feathering range containing interpolation data and extended interpolation data; and
   said feathering circuit feathering data in said feathering range.

28. A device as recited in claim 25, wherein said feathering range includes a cross-over channel.

29. A method of operating an image processing device, comprising:
   generating interpolated data and extended interpolation data; and
   feathering said interpolated data and said extended interpolation data.

30. A method as recited in claim 29, comprising:
   feathering said data using feathering weights W1 and W2 which satisfy:
   W1 and W2 are continuous functions of n;
   W1(n)+W2(n)=1, for any M1<n<M2;
   W1(M1)=W2(M2)=1; and
   W1($n_c$)=W2($n_c$)=0.5;
      where n is a data channel of said device, $n_c$ is a cross-over channel, and M1 and M2 are first and second threshold channels, respectively.

31. A method as recited in claim 30, comprising:
   using said feathering weights W1 and W2 satisfying W1($n_c$)≈W2($n_c$)≈0.5.

32. A method as recited in claim 30, comprising:
   feathering said data using feathering weights W1 and W2 which satisfy:
   W1 and W2 are continuous functions of d;
   W1(d)+W2(d)=1, for 0<d<$d_{M2}$;
   W1(0)=W2($d_{M2}$)=1; and
   W1($d_c$)=W2($d_c$)=0.5;
where Z(n) is an axial position of a complementary data point at a data channel n of said device, Z(M1) and Z(M2) are axial positions of first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

33. A method as recited in claim 32, comprising:
   using said feathering weights W1 and W2 satisfying W1($d_c$)≈W2($d_c$)≈0.5.

34. A method as recited in claim 29, wherein generating interpolated data and extended interpolation data comprises:
   generating first interpolated data from a first data channel of said device to a cross-over channel;
   generating second interpolated data from a second data channel of said device to said cross-over channel;
   generating first extended interpolation data from said cross-over channel to a first threshold channel;
   generating second extended interpolation data from said cross-over channel to a second threshold channel; and
   feathering using first and second interpolation data and first and second extended interpolation data between said first and second threshold channels.

35. A method as recited in claim 34, comprising:
   feathering said data using feathering weights W1 and W2 which satisfy:
   W1 and W2 are continuous functions of n;
   W1(n)+W2(n)=1, for any M1<n<M2;
   W1(M1)=W2(M2)=1; and
   W1($n_c$)=W2($n_c$)=0.5;
      where n is a data channel of said device, $n_c$ is said cross-over channel, and M1 and M2 are said first and second threshold channels, respectively.

36. A method as recited in claim 35, comprising:
   using said feathering weights W1 and W2 satisfying W1($n_c$)≈W2($n_c$)≈0.5.

37. A method as recited in claim 34, comprising:
   feathering said data using feathering weights W1 and W2 which satisfy:
   W1 and W2 are continuous functions of d;
   W1(d)+W2(d)=1, for 0<d<$d_{M2}$;
   W1(0)=W2($d_{M2}$)=1; and
   W1($d_c$)=W2($d_c$)=0.5;
where Z(n) is an axial position of a complementary data point at a data channel n of said device, Z(M1) and Z(M2) are axial positions of said first and second threshold channels M1 and M2, respectively, d is a distance Z(n)−Z(M1), $d_c$ is a cross-over distance Z(D2)−Z(M1), and $d_{M2}$ is a distance Z(M2)−Z(M1).

38. A method as recited in claim 36, comprising:
   using said feathering weights W1 and W2 satisfying W1($d_c$)≈W2($d_c$)≈0.5.

39. A method as recited in claim 29, comprising:
   generating first interpolation data;
   generating second interpolation data being discontinuous with said first interpolation data;

generating extended interpolation data about said discontinuity; and feathering said first and second interpolation data using said extended interpolation data to produce data continuous with said first and second interpolation data.

40. A method as recited in claim 39, comprising:

generating said second interpolation data being discontinuous with said first interpolation data at a cross-over point; and generating said extended interpolation data about said cross-over point.

41. A method as recited in claim 39, comprising:

generating first extended interpolation data as an extension of said first interpolation data; and generating second extended interpolation data as an extension of said second interpolation data.

42. A method as recited in claim 41, comprising:

generating said first extended interpolation data to overlap a portion of said second interpolation data;

generating said second extended interpolation data to overlap a portion of said first interpolation data; and feathering using said overlapped portions of said first and second interpolation data and said first and second extended interpolation data.

43. A method as recited in claim 42, comprising:

feathering said overlapped portion of said first interpolation data with said second extended interpolation data; and feathering said overlapped portion of said second interpolation data with said first extended interpolation data.

44. A method as recited in claim 39, comprising:

using feathering weights satisfying one of first and second sets of conditions, said first set comprising:
W1 and W2 are continuous functions of n,
$W1(n)+W2(n)=1$, for any $M1<n<M2$,
$W1(M1)=W2(M2)=1$, and
$W1(n_c)=W2(n_c)=0.5$; and said second set comprising:
W1 and W2 are continuous functions of d,
$W1(d)+W2(d)=1$, for $0<d<d_{M2}$,
$W1(0)=W2(d_{M2})=1$, and
$W1(d_c)=W2(d_c)=0.5$;
where n is a data channel of said device, $n_c$ is a cross-over channel, and M1 and M2 are first and second threshold channels, respectively, Z(n) is an axial position of a complementary data point at said channel n, Z(M1) and Z(M2) are axial positions of said first and second threshold channels M1 and M2, respectively, d is a distance Z(n)–Z(M1), $d_c$ is a cross-over distance Z(D2)–Z(M1), and $d_{M2}$ is a distance Z(M2)–Z(M1).

45. A method as recited in claim 29, comprising:

generating first and second interpolation data;

generating first extended interpolation data as an extension of said first interpolation data;

generating second extended interpolation data as an extension of said second interpolation data; and feathering using said first and second interpolation data and said first and second extended interpolation data.

46. A method as recited in claim 45, comprising:

generating said first and second extended interpolation data each extending from a discontinuity between said first and second interpolation data.

47. A method as recited in claim 46, comprising:

using feathering weights satisfying one of first and second sets of conditions, said first set comprising:
W1 and W2 are continuous functions of n,
$W1(n)+W2(n)=1$, for any $M1<n<M2$,
$W1(M1)=W2(M2)=1$, and
$W1(n_c)=W2(n_c)=0.5$; and said second set comprising:
W1 and W2 are continuous functions of d,
$W1(d)+W2(d)=1$, for $0<d<d_{M2}$,
$W1(0)=W2(d_{M2})=1$, and
$W1(d_c)=W2(d_c)=0.5$;
where n is a data channel of said device, $n_c$ is a cross-over channel, and M1 and M2 are first and second threshold channels, respectively, Z(n) is an axial position of a complementary data point at said channel n, Z(M1) and Z(M2) are axial positions of said first and second threshold channels M1 and M2, respectively, d is a distance Z(n)–Z(M1), $d_c$ is a cross-over distance Z(D2)–Z(M1), and dm is a distance Z(M2)–Z(M1).

48. A computer program product, comprising:

a computer storage medium and a computer program code mechanism embedded in the computer storage medium for processing an image generated in an image processing apparatus, the computer program code mechanism comprising:

a first computer code device configured to generate interpolated data and extended interpolation data; and a second computer code device configured to feather said interpolated data and said extended interpolation data.

49. A computer program product as recited in claim 48, comprising:

said second computer code device configured to feather said data using feathering weights W1 and W2 which satisfy:
W1 and W2 are continuous functions of n;
$W1(n)+W2(n)=1$, for any $M1<n<M2$;
$W1(M1)=W2(M2)=1$; and
$W1(n_c)=W2(n_c)=0.5$;
where n is a data channel of said apparatus, $n_c$ is a cross-over channel, and M1 and M2 are first and second threshold channels, respectively.

50. A computer program product as recited in claim 49, comprising:

said second computer code device configured to use said feathering weights W1 and W2 satisfying $W1(n_c) \approx W2(n_c)$ 0.5.

51. A computer program product as recited in claim 48, comprising:

said second computer code device configured to feather said data using feathering weights W1 and W2 which satisfy:
W1 and W2 are continuous functions of d;
$W1(d)+W2(d)=1$, for $0<d<d_{M2}$;
$W1(0)=W2(d_{M2})=1$; and
$W1(d_c)=W2(d_c)=0.5$;
where Z(n) is an axial position of a complementary data point at a data channel n of said apparatus, Z(M1) and Z(M2) are axial positions of first and second threshold channels M1 and M2, respectively, d is a distance Z(n)–Z(M1), $d_c$ is a cross-over distance Z(D2)–Z(M1), and $d_{M2}$ is a distance Z(M2)–Z(M1).

52. A computer program product as recited in claim 51, comprising:

said second computer code device configured to use said feathering weights W1 and W2 satisfying $W1(n_c) \approx W2(n_c) \approx 0.5$.

53. A computer program product as recited in claim 48, comprising:
   a third computer code device configured to generate first interpolated data from a first data channel of said apparatus to a cross-over channel;
   a fourth computer code device configured to generate second interpolated data from a second data channel of said apparatus to said cross-over channel;
   a fifth computer code device configured to generate first extended interpolation data from said cross-over channel to a first threshold channel;
   a sixth computer code device configured to generate second extended interpolation data from said cross-over channel to a second threshold channel; and
   a seventh computer code device configured to feather using first and second interpolation data and first and second extended interpolation data between said first and second threshold channels.

54. A computer program product as recited in claim 48, comprising:
   a third computer code device configured to generate first interpolation data;
   a fourth computer code device configured to generate second interpolation data being discontinuous with said first interpolation data;
   a fifth computer code device configured to generate extended interpolation data about said discontinuity; and
   a sixth computer code device configured to feather said first and second interpolation data using said extended interpolation data to produce data continuous with said first and second interpolation data.

55. A computer program product as recited in claim 48, comprising:
   a third computer code device configured to generate first and second interpolation data;
   a fourth computer code device configured to generate first extended interpolation data as an extension of said first interpolation data;
   a fifth computer code device configured to generate second extended interpolation data as an extension of said second interpolation data; and
   a sixth computer code device configured to feather using said first and second interpolation data and said first and second extended interpolation data.

* * * * *